US007875011B2

(12) United States Patent
Harvie

(10) Patent No.: US 7,875,011 B2
(45) Date of Patent: Jan. 25, 2011

(54) COOLING, HEATING, BLADDER RELIEF, GAS, HYDRATION AND NUTRITION CHEM-BIO SUIT CONNECTIVITY SYSTEM

(76) Inventor: Mark R. Harvie, 115 Catamount Dr., Milton, VT (US) 05468

( * ) Notice: Subject to any disclaimer, the term of this patent is extended or adjusted under 35 U.S.C. 154(b) by 468 days.

(21) Appl. No.: 12/077,762

(22) Filed: Mar. 22, 2008

(65) Prior Publication Data

US 2008/0238093 A1 Oct. 2, 2008

Related U.S. Application Data

(63) Continuation-in-part of application No. 11/977,024, filed on Oct. 23, 2007, which is a continuation-in-part of application No. 11/472,162, filed on Jun. 21, 2006, now Pat. No. 7,335,189, which is a continuation-in-part of application No. 11/047,143, filed on Jan. 29, 2005, now Pat. No. 7,141,043, which is a continuation-in-part of application No. 11/005,800, filed on Dec. 7, 2004, now Pat. No. 7,131,964, which is a continuation-in-part of application No. 10/885,355, filed on Jul. 6, 2004, now Pat. No. 7,135,012, which is a continuation-in-part of application No. 10/418,852, filed on Apr. 18, 2003, now Pat. No. 6,918,899, which is a continuation-in-part of application No. 10/369,240, filed on Feb. 19, 2003, now Pat. No. 6,706,027.

(60) Provisional application No. 60/359,672, filed on Feb. 26, 2002.

(51) Int. Cl.
*A61F 5/44* (2006.01)

(52) U.S. Cl. ....................................... 604/355; 4/144.1

(58) Field of Classification Search ................. 604/317, 604/320, 327, 355, 356, 540, 544; 4/144.1–144.4; 600/574, 578–579
See application file for complete search history.

(56) References Cited

U.S. PATENT DOCUMENTS

| | | | | |
|---|---|---|---|---|
| 4,747,166 | A * | 5/1988 | Kuntz | 4/144.1 |
| 6,443,939 | B1 * | 9/2002 | Oki et al. | 604/393 |
| 6,551,293 | B1 * | 4/2003 | Mitchell | 604/353 |
| 6,740,066 | B2 * | 5/2004 | Wolff et al. | 604/319 |
| 7,338,482 | B2 * | 3/2008 | Lockwood et al. | 604/543 |
| 7,390,320 | B2 * | 6/2008 | Machida et al. | 604/320 |
| 2007/0219532 | A1 * | 9/2007 | Karpowicz et al. | 604/540 |

* cited by examiner

*Primary Examiner*—Tatyana Zalukaeva
*Assistant Examiner*—Benedict L Hanrahan
(74) *Attorney, Agent, or Firm*—Eric R. Benson

(57) ABSTRACT

This invention is a Cooling, Heating, Bladder Relief, Gas, Hydration and Nutrition Chem-Bio Suit Connectivity System used connecting various life function support systems in Chemical-Biological Protective Suits. The connectivity system provides means to quick connect and disconnect various user desired support systems including cooling and heating, bladder relief, gas, hydration and nutrition and external to a user that is inside a Chem-Bio Suit. The connectivity system is capable of allowing a user to use any of the support systems either in any combination thereof or individually. The connectivity system self perforates and self seals upon installation in the Chem-Bio Suit and seals upon connection and disconnection of life support systems to prevent contamination from entering inside the Chem-Bio Suit and threatening the health or safety of the user. The connectivity system is easily field installed with no tools required and contains internal electrical, electronic and fiber optic communications capability.

20 Claims, 5 Drawing Sheets

COOLING, HEATING, BLADDER RELIEF, GAS, HYDRATION AND NUTRITION CHEM-BIO SUIT CONNECTIVITY SYSTEM

CROSS REFERENCE TO RELATED APPLICATION

This application is a Continuation-In-Part of the patent application U.S. Ser. No. 11/977,024, filed Oct. 23, 2007, which is in turn a Continuation in Part of the patent application U.S. Ser. No. 11/472,162, filed Jun. 21, 2006 (now issued U.S. Pat. No. 7,335,189), which is in turn a Continuation in Part of the patent application U.S. Ser. No. 11/047,143, filed Jan. 29, 2005 (now issued U.S. Pat. No. 7,141,043), which is in turn a Continuation in Part of the patent application U.S. Ser. No. 11/005,800, filed Dec. 7, 2004 (now issued U.S. Pat. No. 7,131,964), which is in turn a Continuation in Part of the patent application U.S. Ser. No. 10/885,355, filed Jul. 6, 2004 (now issued U.S. Pat. No. 7,135,012), which is in turn a Continuation in Part of the patent application U.S. Ser. No. 10/418,852, filed Apr. 18, 2003 (now issued U.S. Pat. No. 6,918,899), which in turn is a Continuation-In-Part of patent application U.S. Ser. No. 10/369,240 filed Feb. 19, 2003 (now issued U.S. Pat. No. 6,706,027) and claiming priority from Provisional Patent Application No. 60/359,672 which was filed on Feb. 26, 2002, all of which are hereby incorporated by reference as if set forth in their entirety herein.

BACKGROUND ART

Current state of the art Chemical/Biological (CB or Chem-Bio) protective garments do not provide an acceptable and safe means of connecting the garments to external life support systems such as cooling and heating, bladder relief, gas, hydration and nutrition delivery systems without exposing the user to undue risk of exposure to external health and safety threats. The lack of a safe and easy connectivity for these life support systems poses serious risks for their users, which are often individuals involved in some aspect of public safety or military operations. Contributing to the problem of development of an effective connectivity system in these CB applications is the fact that CB Protective Suits have an effective use time of only 24 hours on average depending upon the CB agents that are involved. In many cases if external systems are connected to CB Protective Suits they are installed by crude cuts or tears into the Suit and sealed by duct tape or some other similarly unsafe method.

For body waste management, NASA has developed several systems for use with pressurized suits. These include 1) male urine collection systems consisting of external catheters connected to polymeric containment bags, or garments worn inside the suit, 2) female urine collection systems, consisting of multilayered undergarments with both conductive and super absorbent layers, and 3) fecal containment systems consisting of absorbent undergarments that collect and contain fecal matter until the pressure suit is doffed. These waste management systems, however, have been found to pose an unacceptable psychological demands upon the users, especially in their military applications.

A study by the United States Army was conducted using a retractable-arm design for protective suits. The user of a CB Suit would unzip a bellows located under the arms and retract their arms into the suit, leaving the gloves attached to the sleeves. This would allow greater freedom of movement during waste management procedures. Additionally other options were researched for fecal and urine collection. For fecal collection, the users would use a fecal collection bag for waste. This system was comprised of a fecal collection bag that had a contoured opening that attaches to the perianal area of the user using an adhesive ring. After its use the adhesive ring would then be folded up to form an air-tight seal containing what can be a disagreeable effluent.

For urinary waste, two systems have been developed, one for males and one for females. The system for males utilizes a urine collection device that consists of a 750 to 1000 ml urinary collection bag with an attached latex condom catheter. The system for females uses the same collection bag as the male system but interfaced with an external urethral catheter. Both of these systems in the CB Suit utilize pockets on the interior of the CB Suit to provide storage for the collection bags and other hygiene items.

In testing the extremes of duration for use of this type of waste management system, the urine and fecal collection options were analyzed. Serious problems with the systems were discovered. The collection bags over time resulted in voluminous and forceful voids and some splash-back because the inlet aperture on the urine collection bags were not large enough to handle the rate of flow. The 750 ml storage bag was found to be too small to accommodate larger voids. Despite the fact that the fecal collection system during the test exhibited no spillage or serious problems of note, the total time required to complete the waste management procedure was about 35 minutes, which is entirely unacceptable in an emergency or military setting.

Complicating the waste management problems of CB Suits are the risks involved with heat stress. The perspiration and heat buildup, both from trapped body heat and heat absorption from the environment, is not able to escape the over garments. This condition causes a threat of heat exhaustion and heat stroke. Even the new JSLIST (joint service lightweight integrated suit technology) does not protect against heat stress.

It is known in the art that in high temperatures, the average CB Suit user can do physical work in chemical protective clothing only for a few hours or less, depending on the individual and the external environmental conditions. Research has shown that with forced fluid intake and work-rest cycles, work time can be extended. It has been conclusively demonstrated just how important it is that CB Suit users remain hydrated, especially in high temperature environments. Yet many CB Suit users (i.e. public safety personnel, military personnel) will intentionally dehydrate themselves prior to donning the CB Suits for the express purpose of avoiding the future necessity of relieving their bladders. The effect of dehydration impairs performance and can lead to serious health problems such as painful, incapacitating kidney stones. The symptoms of dehydration include headaches, muscle fatigue, poor decision-making, impaired hand-eye coordination and lightheadedness. The latter can lead to performance degradation, loss of morale, threats to public safety and mission failure. So, a recommended regularized drinking regimen to protect against heat stress will require periodic urination. CB Suits, containing zippers and rear flaps, are poorly designed for waste elimination without the risk of compromising the protective capabilities of the Suit. Most soldiers in training when needing to urinate or defecate while in the presence of a simulated threat will simply unzip and void without the requisite fear of the consequences and expose themselves to harmful agents.

In military uses of CB Suits many soldiers will often urinate and/or defecate in their protective garments. This in turn, wets the charcoal lining which will ultimately compromise the integrity of the suit. Prolonged exposure to fecal matter and urine can cause skin damage. Upon prolonged exposure irritation of the skin appears first and then the skin breakdown occurs. Feces also contain bacteria that can permeate allowing for infections and may progress rapidly to ulcerations, including bacterial and yeast infections. Lastly, constant moisture can alter the skins' protective pH balance.

Avoiding urination can also lead to bladder over distension, pain, trouble emptying, and can eventually lead to urinary incontinence. A full, distended bladder can cause a stretching of the bladder muscle, thus leading to a more floppy bladder which can not contract as well as before being stretched. This imparts some 'laziness'to the bladder to empty properly and can result in lifelong bladder disability.

The relatively short life span of a CB Protective Suit in use (approx. 24 hours) makes it impractical to incorporate within the garment a means of cooling and heating, gas, hydration, nutrition and bladder relief. Also because of the bulk of such life support systems it is not practical to contain these systems inside the Suit along with the user. There is a long felt need for a connection system that can be field installed without tools that will permit the user to connect to whatever external life support systems that may be needed given the circumstances of the use of the Suit.

In many applications where CB Protective Suits are used it would be advantageous to be able to introduce clean air and/or oxygen inside the Suit. By maintaining a positive air pressure in the Suit, which in most instances is not air tight, would significantly reduce the likelihood of outside ambient and potentially hazardous air from entering into the suit. Having connectivity for an external gas source to connect to an internal gas mask further improves the versatility of the Suit and the safety of the user.

While the prior art disclose various systems of providing life support connection to CB Protective Suits which fulfill their respective particular objectives and requirements, and are most likely quite functional for their intended purposes, it will be noticed that none of the prior art cited disclose an apparatus and/or method that allow a user ease of field installation, comfort of automatic operation, easy disposal, sanitary use in the field and large volume capacity, and quick and safe connection and disconnection to several life support systems thereby permitting a user to work several hours in relative comfort and safety. As such, there apparently still exists the need for a new and improved life support connection system to maximize the benefits to the user and minimize the risks of injury from its use.

This optimum connectivity for any life support system would allow a CB Protective Suit user to quickly and sanitarily: urinate; hydrate; breath compressed air; take in a food source; and/or heat or cool their bodies, without the necessity of doffing the Suit or exposing a portion of their body to potentially fatal chemical or biological agents, and to then remove the life support system(s), if desired, that is external to the user without exposure to the elements from which the CB Suit is being used to protect the user. In this respect, the present invention disclosed herein substantially fulfills this need.

DISCLOSURE OF THE INVENTION

In view of the foregoing limitations inherent in the known types of connectivity systems for CB Protective Suits now present in the prior art, the present invention provides an apparatus that has been designed to self-perforate a Suit into which it is being installed and snap fit to the internal interface of the connection device inside the Suit with no tools being required. Once installed the connectivity system allows a user to quick connect, or disconnect, their choice of life support systems, such as cooling and heating, gas, hydration, nutrition and bladder relief. As such, the general purpose of the present invention, which will be described subsequently in greater detail, is to provide a field designed apparatus and method of use that incorporates the present invention.

The present invention also incorporates electric, electronic and fiber optics to facilitate communication and control of the various life support systems electronically. There can be multiple communication transmission lines made of various materials including aluminum, copper, nickel, silver, gold, USB cable, coaxial cable or the like. This permits transmission of vital signs and control of systems to a remote location where a user's activities may be monitored and regulated. It also permits the life support systems to be controlled automatically at pre-selected or default settings. There are many additional novel features directed to solving problems not addressed in the prior art.

To attain this, the present invention generally comprises an external face plate with quick connects/disconnects capable of connecting to, or disconnecting from, user selected life support systems such as 1) nutrition; 2) hydration and bladder relief combination devices such as disclosed and hereby incorporated by reference in my prior patent U.S. Pat. No. 7,141,043 or a stand alone hydration source; 3) bladder relief devices such as disclosed and hereby incorporated by reference as set forth in my prior patents U.S. Pat. Nos. 7,335,189, 7,135,012, 7,131,964, 6,918,899 and 6,706,027; 4) personal cooling and heating devices such as disclosed and hereby incorporated by reference as set forth in my prior patents U.S. Pat. Nos. 6,915,641 and 7,152,412; and 5) air and/or oxygen. The external face plate is fitted with a cutting means that when placed against the surface of a CB Protective Suit and pressure is applied the external face plate perforates the Suit. Once perforated the external face plate is gasketed on the external portion or outside of the CB Protective Suit. Inside the CB Protective Suit is an internal face plate that is also gasketed on the internal portion or inside of the CB Protective Suit which is designed to accept the locking tabs of the external face plate that enter into the Suit through the perforation and snap fit together with the internal face plate. Once snap fit together the gaskets form an air/liquid tight seal and the external and internal face plates form one or more fluid and/or air tight channels capable of passing fluids or gases from outside the Suit to the inside. The internal face plate also has quick connect/disconnect fittings that allow the internal connections necessary to deliver the life support system to the user as needed. Inside the CB Protective Suit the internal face plate may connect: 1) the gas port of the connectivity device to a gas mask or simply permit the gas to enter into the Suit; 2) to the male or female urine collection means such as those described in my patent disclosures hereby incorporated by reference as set forth in U.S. Pat. Nos. 7,335,189, 7,135,012, 7,131,964, 6,918,899 and 6,706,027; 3) to a heating and cooling vest or garment such as that disclosed and hereby incorporated by reference as set forth in my prior patents U.S. Pat. Nos. 6,915,641 and 7,152,412 and U.S. patent application No. 12/070,435 filed on Feb. 19, 2008; 4) to a hose and/or mouthpiece accessible to a user for drinking; and 5) to a hose and/or mouthpiece accessible to a user for eating by means of liquid nutrition.

Several objects and advantages of the present invention are:

in the preferred embodiment of the present invention the connectivity system may be easily installed in the field without tools by self perforating the CB Protective Suit in a location that best meets the user's needs in the most preferred embodiment the connectivity system can connect one or more external life support systems to the CB Protective Suit which include heating and cooling, gas (generally compressed air), a hydration source (i.e. water or electrolyte enhanced hydrator), a nutrition source (i.e. a nutrient rich liquid like Ensure® or other liquid complete nutrition source), and a urine transport and collection means in the most preferred embodiment the connectivity system is lightweight, relatively small device of a relatively low cost which is important given that it will most likely be disposed off with the CB Protective Suit after its use since CB Protective Suits only last for a relatively short period of time, whereas the external life support systems and the internal user connections can be quickly and easily disconnected for use on another CB Protective Suit.

in the most preferred embodiment the connectivity system contains electric, electronic and fiber optic lines to connect the external life support systems to the user interface life support devices to facilitate monitoring and control of the needs and delivery of life support to a user. The lines can also be used to connect radio, wireless or other telephonic communication capability to a user.

These together with other objects of the invention, along with the various features of novelty which characterize the invention, will be pointed out with particularity in the claims which are annexed to and form a part of this patent application. For a better understanding of the invention, its operating advantages and the specific objects attained by its uses, reference should be had to the accompanying drawings and descriptive matter in which there is illustrated preferred embodiments of the invention.

BEST MODES FOR CARRYING OUT THE INVENTION

I. Preferred Embodiments

Figure 1:
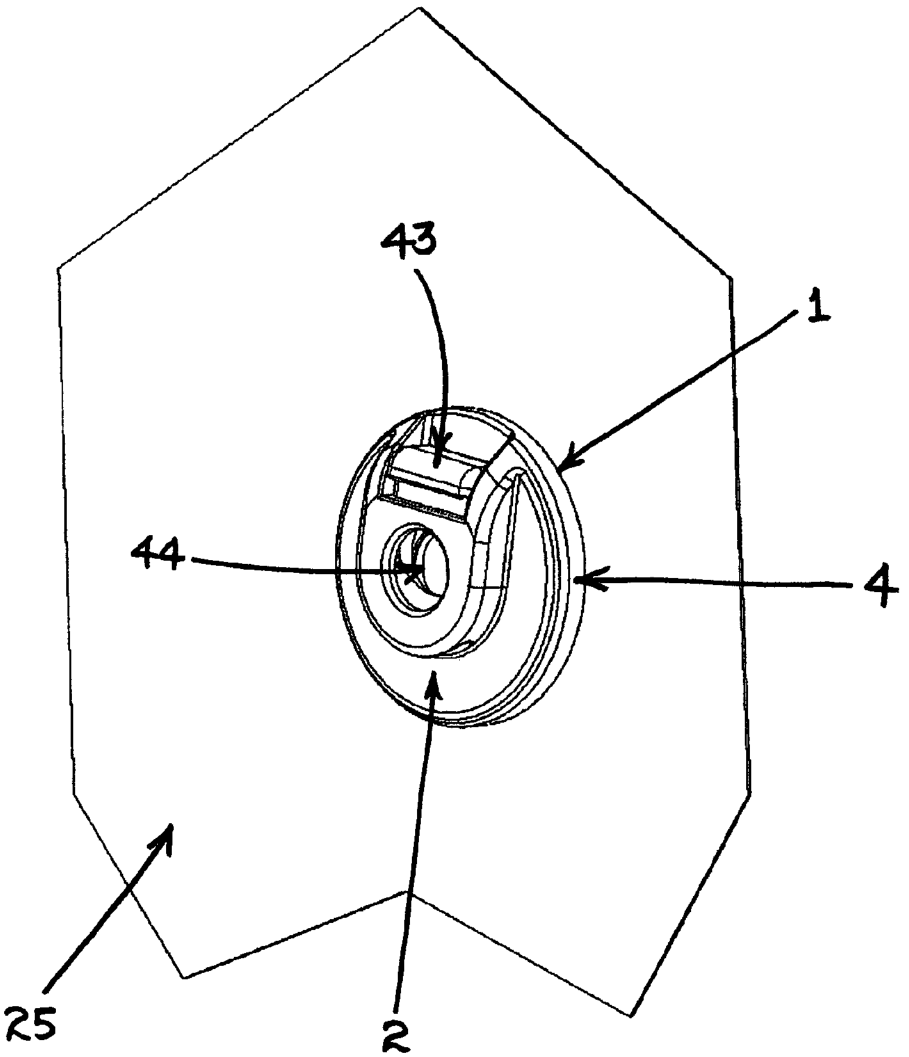
FIG. 1 is a perspective view of the external face plate of the connectivity system installed into a cut away view of a CB Protective Suit.
Figure 2:
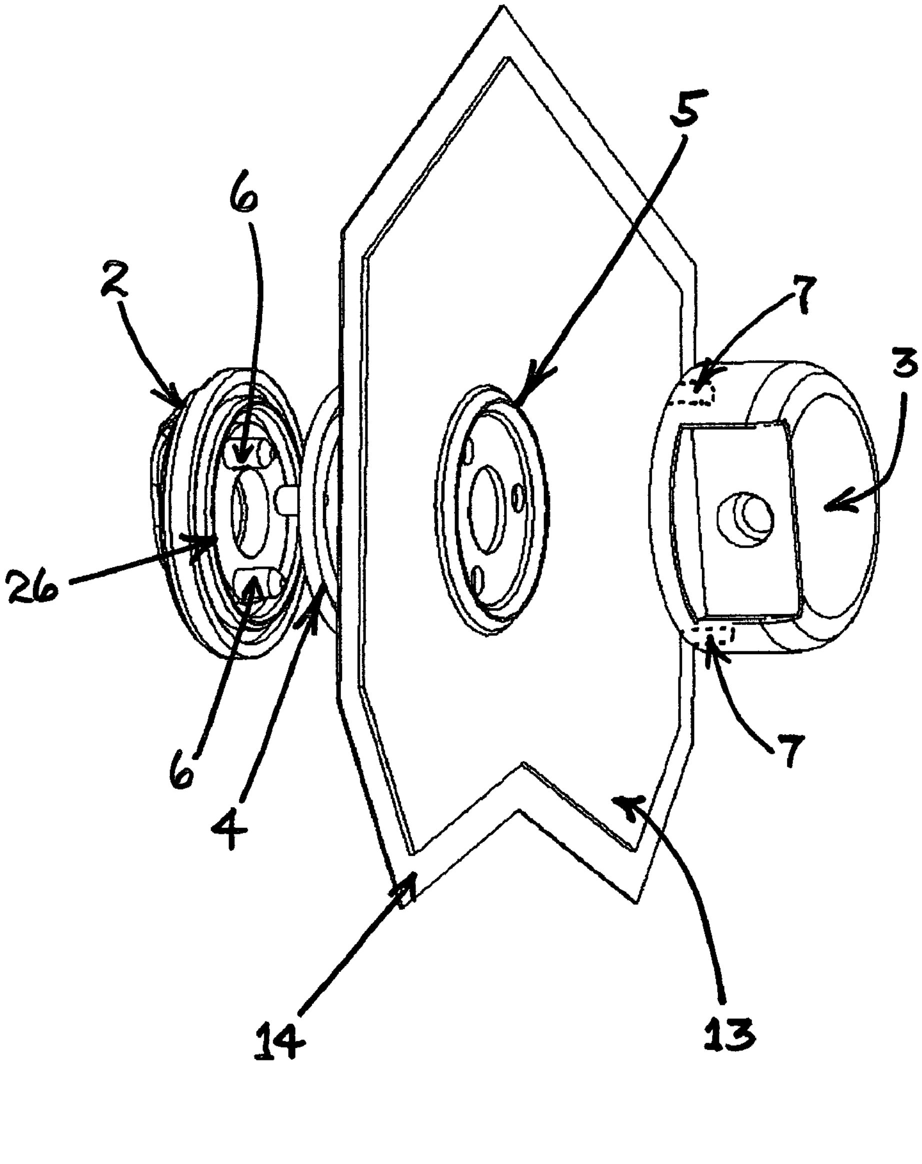
FIG. 2 is an exploded perspective view of the connectivity system as it would be installed into a cut away view of a CB Protective Suit from the perspective of the internal face of the CB Protective Suit with a perspective view of the internal face plate also depicted.
Figure 3:
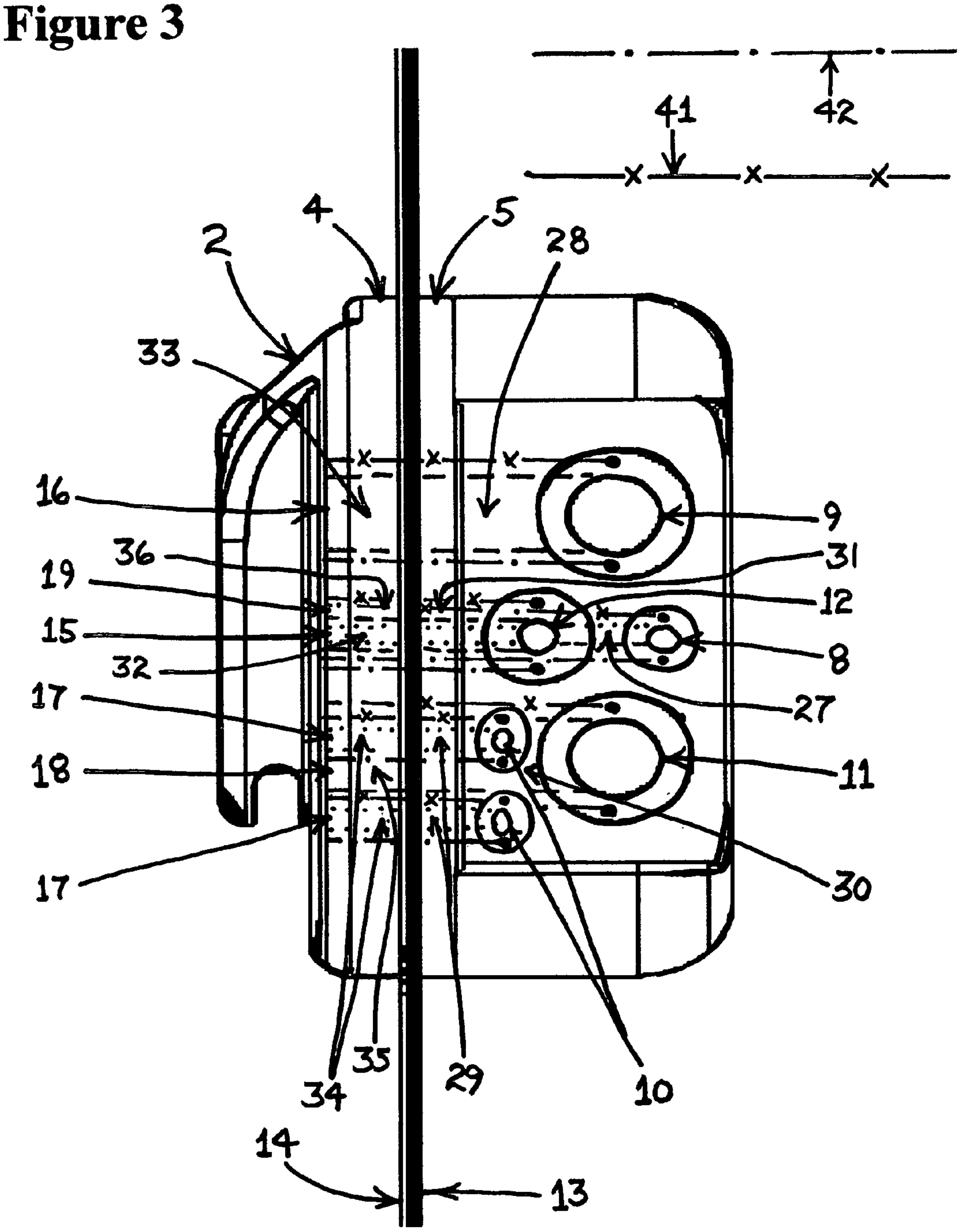
FIG. 3 is a side view of the connectivity system as it would be installed into a cut away view of a CB Protective Suit.

With reference now to the drawings, and in particular to FIGS. 1-4 thereof, a new and novel cooling, heating, bladder relief, gas, hydration and nutrition chem-bio suit connectivity system embodying the principles and concepts of the present invention and generally designated by the reference numeral 1.

List and Description of:

GENERAL DESCRIPTION OF REFERENCE NUMERALS IN THE DESCRIPTION AND DRAWINGS

Any actual dimensions listed are those of the preferred embodiment. Actual dimensions or exact hardware details and means may vary in a final product or most preferred embodiment and should be considered means for so as not to narrow the claims of the patent.

(1) Connectivity Device
(2) External Face Plate
(3) Internal Face Plate
(4) External Gasket
(5) Internal Gasket
(6) Locking Tab
(7) Locking Tab Receptor
(8) Inner Gas Port
(9) Inner Hydration Port
(10) Inner Cooling and Heating Port
(11) Inner Nutrition Port
(12) Inner Urine Disposal Port
(13) CB Protective Suit Inner Layer
(14) CB Protective Suit Outer Layer
(15) Outer Gas Port
(16) Outer Hydration Port
(17) Outer Cooling and Heating Port
(18) Outer Nutrition Port
(19) Outer Urine Disposal Port
(20) Gas Storage and Delivery Means
(21) Hydration Storage and Delivery Means
(22) Nutrition Storage and Delivery Means
(23) Cooling and Heating Means
(24) Urine Disposal Means
(25) CB Protective Suit
(26) Cutting Means
(27) Inner Gas Channel
(28) Inner Hydration Channel
(29) Inner Cooling and Heating Channel
(30) Inner Nutrition Channel
(31) Inner Urine Disposal Channel
(32) Outer Gas Channel
(33) Outer Hydration Channel
(34) Outer Cooling and Heating Channel
(35) Outer Nutrition Channel
(36) Outer Urine Disposal. Channel
(37) User Life Support Hose
(38) Gas Mask
(39) Mouthpiece Valve
(40) Urine Collection Device
(41) Fiber Optic Line
(42) Electrical-Electromagnetic Line
(43) Quick Connect-Disconnect Locking Slide and Release
(44) Hose Connector Socket Inlet
(45) External Input Connector Fitting
(46) Internal Input Connector Fitting
(47) Hose and Line Protector Sleeve
(48) Electrical-Electronic and Fiber Optic Connector
(49) Heating and Cooling Vest

DETAILED DESCRIPTION OF THE PREFERRED EMBODIMENT

1. Connectivity Device

The Connectivity Device (1) is generally comprised of five major components: 1) an External Face Plate (2); 2) an Internal Face Plate (3); 3) an External Gasket (4); an Internal Gasket (5); and 5) a Cutting Means (26). The External Face Plate (2) is further comprised of one or more life support connection ports, namely an Outer Gas Port (15), Outer Hydration Port (16), Outer Cooling and Heating Port (17), Outer Nutrition Port (18), and an Outer Urine Disposal Port (19). The connection ports are generally comprised of self-sealing quick disconnect fittings. The External Face Plate (2) is further comprised of one or more channels that are capable of having transported there through life support means, said channels being namely an Outer Gas Channel (32), Outer Hydration Channel (33), Outer Cooling and Heating Channel (34), Outer Nutrition Channel (35), and an Outer Urine Disposal Channel (36).

Once the Connectivity Device (1) is completely assembled and installed for use the life support connection ports may then be connected to one or more user selected life support means, namely a Gas Storage and Delivery Means (20), Hydration Storage and Delivery Means (21), Nutrition Storage and Delivery Means (22), Cooling and Heating Means (23), and a Urine Disposal Means (24).

The Cutting Means (26) is disposed in the External Face Plate (2) such that when the sharp edge of the Cutting Means (26) is applied with pressure generally applied by the palm of the hand of the installer against the CB Protective Suit (25) the Cutting Means (26) perforates the CB Protective Suit (25). Once the CB Protective Suit (25) is perforated the External Face Plate (2) is placed against the External Gasket (4) which in turn is placed against the CB Protective Suit Outer Layer (14) forming a seal thereby.

The Internal Face Plate (3) is further comprised of one or more user interfaced life support connection ports, namely an Inner Gas Port (8), Inner Hydration Port (9), Inner Cooling and Heating Port (10), Inner Nutrition Port (11), and an Inner Urine Disposal Port (12). The Internal Face Plate (3) is further comprised of one or more channels that are capable of having transported there through life support means, said channels being namely an Inner Gas Channel (27), Inner Hydration Channel (28), Inner Cooling and Heating Channel (29), Inner Nutrition Channel (30), and an Inner Urine Disposal Channel (31).

Once the Connectivity Device (1) is completely assembled and installed for use the user interfaced life support connection ports may then be connected to one or more user selected life support user interface means by means of one or more User Life Support Hoses (37) to: a Gas Mask (38); a Mouthpiece Valve (39); and/or a Urine Collection Device (40).

To assemble the Connectivity Device (1) the Internal Face Plate (3) is placed against the Internal Gasket (5) which in turn is placed against the CB Protective Suit Inner Layer (13) forming a seal thereby. Assembly is achieved by placing the External Face Plate (2) against the External Gasket (4) which is placed over, and completely concealing, the perforation of the CB Protective Suit (25) and against the CB Protective Suit Outer Layer (14). Then the Locking Tabs (6) and the Outer Gas Channel (32), Outer Hydration Channel (33), Outer Cooling and Heating Channel (34), Outer Nutrition Channel (35), and an Outer Urine Disposal Channel (36) are aligned through the perforation to the corresponding Locking Tab Receptors (7) and the corresponding Inner Gas Channel (27), Inner Hydration Channel (28), Inner Cooling and Heating Channel (29), Inner Nutrition Channel (30), and an Inner Urine Disposal Channel (31) of the Internal Face Plate (3). The Internal Gasket (5) is placed between the Internal Face Plate (3) and the CB Protective Suit Inner Layer (13). Assembly is completed by locking the corresponding Locking Tabs (6) into the Locking Tab Receptors (7) such that the inner and outer channels form a seal and create continuous channels through the Connectivity Device (1).

To use the Connectivity Device (1) the user selects what life support systems they desire to use, such as the Gas Storage and Delivery Means (20), Hydration Storage and Delivery Means (21), Nutrition Storage and Delivery Means (22), Cooling and Heating Means (23), and the Urine Disposal Means (24) and then connects them by means of the quick disconnect fittings of the corresponding Outer Gas Port (15), Outer Hydration Port (16), Outer Cooling and Heating Port (17), Outer Nutrition Port (18), and the Outer Urine Disposal Port (19). Then based upon the user selected life support systems the user connects by means of the quick disconnect fittings the User Life Support Hose (37), Gas Mask (38), Mouthpiece Valve (39), and the Urine Collection Device (40) to the corresponding Inner Gas Port (8), Inner Hydration Port (9), Inner Cooling and Heating Port (10), Inner Nutrition Port (11), and the Inner Urine Disposal Port (12).

Figure 4:
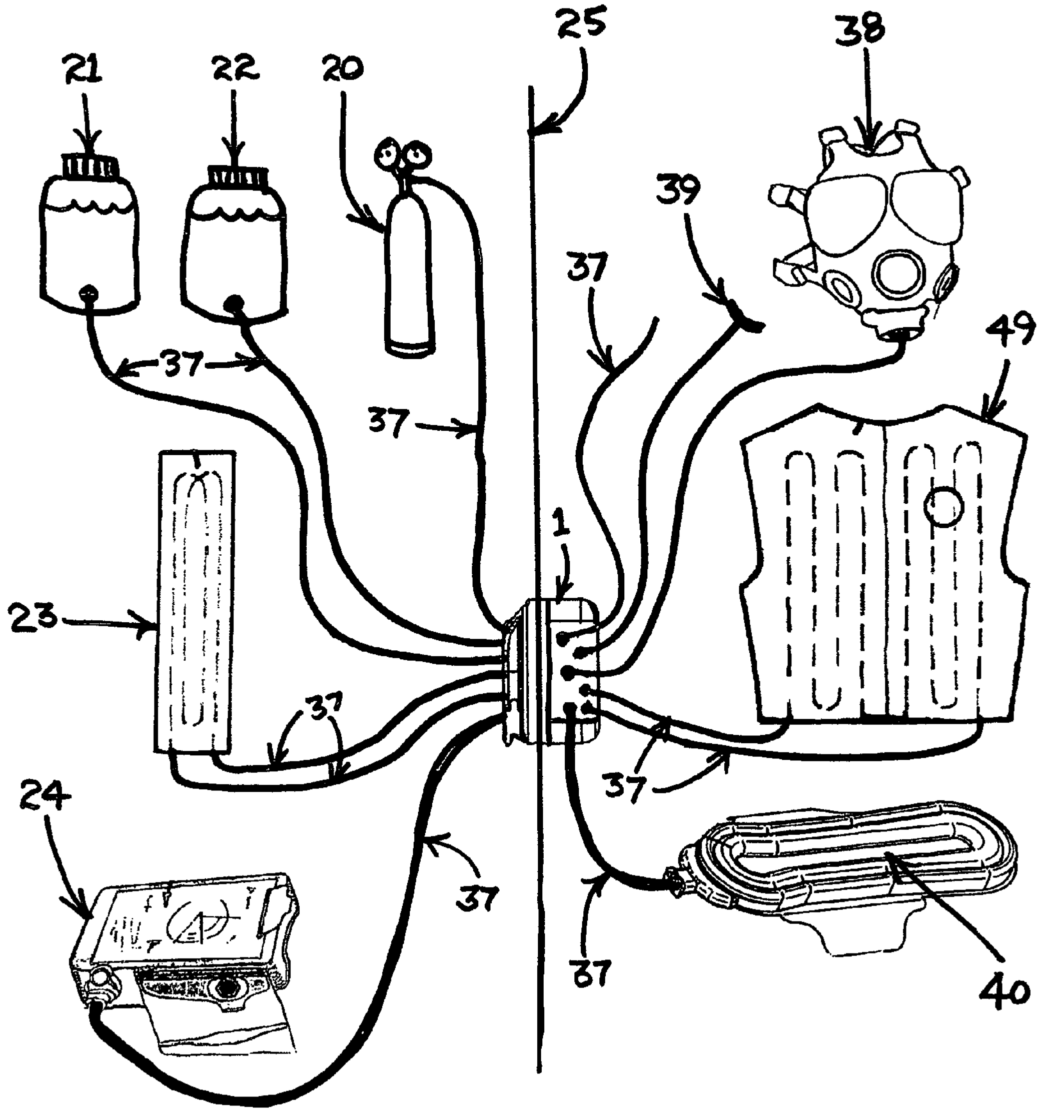
FIG. 4 is a perspective view of the connectivity system with the cooling, heating, bladder relief, gas, hydration and nutrition life support systems and user connection means attached to a cut way view of a CB Protective Suit for use.

FIG. 4 depicts the Connectivity Device (1) external to the CB Protective Suit (25) connected to five life support systems including a Gas Storage and Delivery Means (20), Hydration Storage and Delivery Means (21), Nutrition Storage and Delivery Means (22), Cooling and Heating Means (23), and a Urine Disposal Means (24) connected by means of the User Life Support Hose (37). FIG. 4 further depicts the Connectivity Device (1) internal to the CB Protective Suit (25) which connects the external life support systems to corresponding five internal life support systems including a Gas Mask (38), User Life Support Hose (37), Mouthpiece Valve (39), Heating and Cooling Vest (49) and the Urine Collection Device (40).

Figure 5:
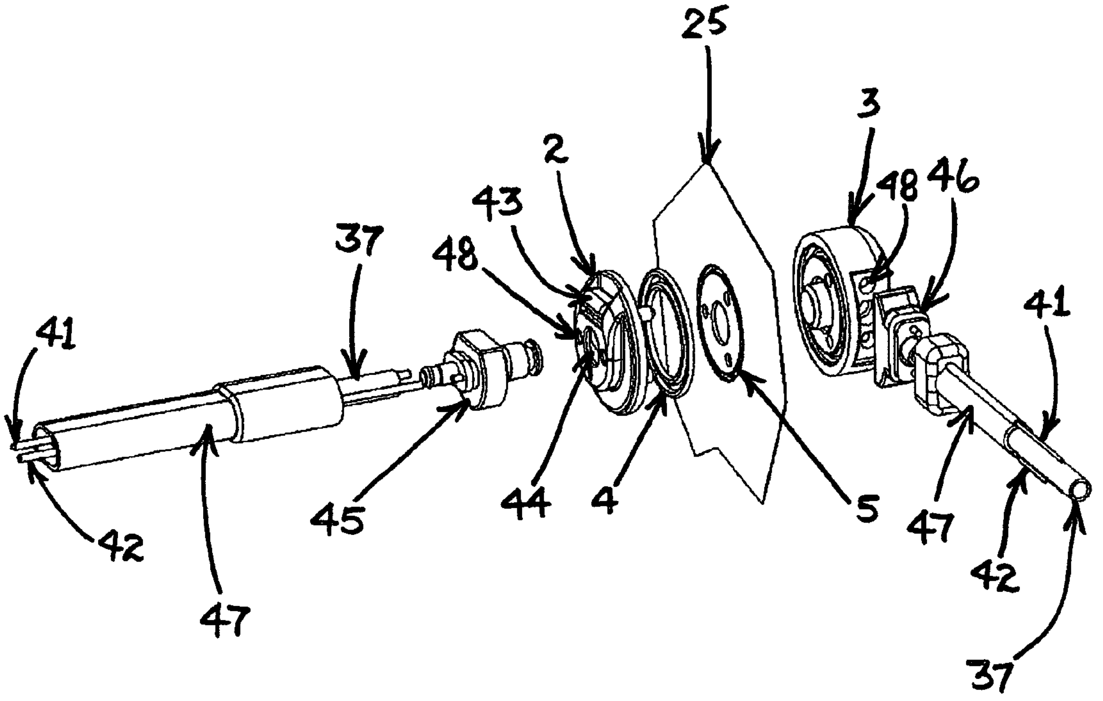
FIG. 5 is a perspective cut away and exploded view of a single life support embodiment of the connectivity system with electrical, electronic and fiber optic communication systems as installed in a cut away view of a CB Protective Suit.

In the most preferred embodiment depicted in FIG. 5 the Connectivity Device (1) incorporates electric, electronic and fiber optic connectivity from the external life support systems to the internal life support systems by means of the Fiber Optic Line (41) and the Electrical-Electromagnetic Line (42). The Fiber Optic Line (41) and the Electrical-Electromagnetic Line (42) are connected through the Connectivity Device (1) by means of the Electrical-Electronic and Fiber Optic Connector (48). The user selected external and internal life support system(s) is connected to the Connectivity Device (1) by a User Life Support Hose (37), the Fiber Optic Line (41) and the Electrical-Electromagnetic Line (42), all of which are protected by a Hose and Line Protector Sleeve (47) connect to the Connectivity Device (1) by means of the Quick Connect-Disconnect Locking Slide and Release (43). The User Life Support Hose (37), the Fiber Optic Line (41) and the Electrical-Electromagnetic Line (42) are attached to the External Input Connector Fitting (45) on the external side of the Connectivity Device (1) and the Internal Input Connector Fitting (46) on the internal side of the Connectivity Device (1). Connection of the life support systems is completed to the Connectivity Device (1) by plugging the External Input Connector Fitting (45) on the external side of the Connectivity Device (1) into the Hose Connector Socket Inlet (44) locking in place by means of the Quick Connect-Disconnect Locking Slide and Release (43), and by also plugging the Internal Input Connector Fitting (46) on the internal side of the Connectivity Device (1) into the Hose Connector Socket Inlet (44) thereby forming a leak proof connection through the channel in the Connectivity Device (1) to both the internal and external User Life Support Hoses (37) and completing the communication circuit of the internal and external Fiber Optic Lines (41) and Electrical-Electromagnetic Lines (42) by means of the Electrical-Electronic and Fiber Optic Connector (48).

While my above descriptions of the invention, its parts, and operations contains many specificities, these should not be construed as limitations on the scope of the invention, but rather as exemplifications of present embodiments thereof. Many other variations are possible, for example, other embodiments, shapes, and sizes of the device can be constructed to fit on a user and work with a unit designed to work by the principles of the present invention; various materials, pumps, colors and configurations can be employed in the unit's design that would provide interesting embodiment differences to users including such practical designs as would, for instance conceal the unit.

Accordingly, the scope of the invention should be determined not by the embodiments illustrated, but by the claims and their legal equivalents as filed herewith.

I claim:

1. A cooling, heating, bladder relief, gas, hydration and nutrition chem-bio suit connectivity system comprised of:

an external face plate;

the external face plate having a life support connection side and a chem-bio protective suit side;

the life support connection side having at least one life support connection means;

the external face plate having at least one life support channel that passes through the external face plate from the life support connection side to the chem-bio protective suit side;

at least one locking tab attached to the external face plate on the chem-bio protective suit side;

a cutting means attached to the external face plate on the chem-bio protective suit side such that when the cutting means contacts the external surface of a chem-bio protective suit and pressure is applied to the life support connection side of the external face plate the chem-bio protective suit is perforated thereby;

an external gasket between the external face plate and the external surface of the chem-bio protective suit forming a seal thereby;

an internal face plate;

the internal face plate having a user interface side and an interior chem-bio protective suit side;

the interior chem-bio protective suit side having at least one life support user connection means;

the internal face plate having at least one life support channel that passes through the internal face plate from the user interface side to the interior chem-bio protective suit side wherein the life support channel of the internal face plate aligns with the life support channel of the external face plate once assembled forming a seal thereby further forming a completed life support channel capable of having gases or fluids pass through the completed life support channel;

an internal gasket between the internal face plate and the internal surface of the chem-bio protective suit forming a seal thereby;

at least one locking tab receptor attached to the internal face plate on the interior chem-bio protective suit side wherein the locking tab receptor of the internal face plate aligns with the locking tab of the external face plate once assembled wherein as assembled the locking tab locks into the locking tab receptor;

at least one life support means removably attached to the life support connection means wherein a source of life support may pass through the life support connection means and the completed life support channel;

at least one user life support interface means removably attached to the life support user connection means wherein a source of life support may pass through the life support user connection means to or from the user;

at least one communication transmission means.

2. The cooling, heating, bladder relief, gas, hydration and nutrition chem-bio suit connectivity system of claim 1 wherein the life support means is a source of hydration.

3. The cooling, heating, bladder relief, gas, hydration and nutrition chem-bio suit connectivity system of claim 1 wherein the life support means is a source of nutrition.

4. The cooling, heating, bladder relief, gas, hydration and nutrition chem-bio suit connectivity system of claim 1 wherein the life support means is a source of air.

5. The cooling, heating, bladder relief, gas, hydration and nutrition chem-bio suit connectivity system of claim 1 wherein the life support means is a source of heating.

6. The cooling, heating, bladder relief, gas, hydration and nutrition chem-bio suit connectivity system of claim 1 wherein the life support means is a source of cooling.

7. The cooling, heating, bladder relief, gas, hydration and nutrition chem-bio suit connectivity system of claim 1 wherein the life support means is a means of urine transport and storage.

8. The cooling, heating, bladder relief, gas, hydration and nutrition chem-bio suit connectivity system of claim 1 wherein the user life support interface means is an open gas port.

9. The cooling, heating, bladder relief gas, hydration and nutrition chem-bio suit connectivity system of claim 1 wherein the user life support interface means is a gas mask.

10. The cooling, heating, bladder relief, gas, hydration and nutrition chem-bio suit connectivity system of claim 1 wherein the user life support interface means is a hose.

11. The cooling, heating, bladder relief, gas, hydration and nutrition chem-bio suit connectivity system of claim 10 wherein the hose has a valve means.

12. The cooling, heating, bladder relief, gas, hydration and nutrition chem-bio suit connectivity system of claim 1 wherein the user life support interface means is a heating and cooling vest.

13. The cooling, heating, bladder relief, gas, hydration and nutrition chem-bio suit connectivity system of claim 1 wherein the user life support interface means is a heating and cooling means attached to the internal surface of the chem-bio protective suit.

14. The cooling, heating, bladder relief, gas, hydration and nutrition chem-bio suit connectivity system of claim 1 wherein the user life support interface means is a urine collection means.

15. The cooling, heating, bladder relief, gas, hydration and nutrition chem-bio suit connectivity system of claim 1 wherein the communication transmission means is fiber optic cable.

16. The cooling, heating, bladder relief, gas, hydration and nutrition chem-bio suit connectivity system of claim 1 wherein the communication transmission means is a conductive cable selected from the group of conductors including aluminum, copper, nickel, silver, or gold.

17. The cooling, heating, bladder relief, gas, hydration and nutrition chem-bio suit connectivity system of claim 1 wherein the communication transmission means is a USB cable.

18. The cooling, heating, bladder relief, gas, hydration and nutrition chem-bio suit connectivity system of claim 1 wherein the communication transmission means is a coaxial cable.

19. The cooling, heating, bladder relief, gas, hydration and nutrition chem-bio suit connectivity system of claim 1 wherein the communication transmission means is a cable carrying a telephonic signal.

20. The cooling, heating, bladder relief, gas, hydration and nutrition chem-bio suit connectivity system of claim 1 wherein the communication transmission means is a cable carrying a radio signal.

* * * * *